United States Patent [19]

Davey et al.

[11] Patent Number: 4,860,735
[45] Date of Patent: Aug. 29, 1989

[54] DRILL ALIGNMENT GUIDE FOR OSTEOPLASTIC SURGERY

[75] Inventors: John R. Davey, Toronto, Canada; William H. Harris, Belmont, Mass.

[73] Assignee: The General Hospital Corporation, Boston, Mass.

[21] Appl. No.: 229,633

[22] Filed: Aug. 8, 1988

[51] Int. Cl.$^4$ .............................................. A61B 17/56
[52] U.S. Cl. ........................... 128/92 V; 128/92 VD; 128/92 VP; 408/72 R; 408/103; 408/110; 408/712
[58] Field of Search .......... 128/92 V, 92 VD, 92 VL, 128/92 VJ, 83; 408/87, 88, 103, 104, 110, 112, 712, 72 R

[56] References Cited

U.S. PATENT DOCUMENTS

| | | | |
|---|---|---|---|
| 2,200,120 | 5/1940 | Nauth | 408/110 X |
| 2,439,803 | 4/1948 | Giesen | 128/92 V X |
| 2,675,003 | 4/1954 | Veley | 408/112 X |
| 2,849,900 | 9/1958 | Heidtman, Jr. | 408/112 |
| 3,060,769 | 10/1962 | Heider | 408/712 X |
| 3,867,932 | 2/1975 | Huene | 128/92 V |

Primary Examiner—Robert A. Hafer
Assistant Examiner—Kevin G. Rooney
Attorney, Agent, or Firm—Lahive & Cockfield

[57] ABSTRACT

A drill alignment apparatus for a drill adapted for osteoplastic surgery comprises an alignment rod mounted thereto and a clamp element. The alignment rod is parallel to and disposed a predetermined distance (D) from a shaft of the drill. The clamp element includes an aperture which permits passage of the rod. The clamp element is adapted to be affixed to a bone, such as a femur, so that the aperture is displaced from the central axis of the bone by substantially the same distance which the center axis of the alignment rod is displaced from the center axis of the drill shaft. When drilling is commenced, the forward end of the alignment rod is placed within the aperture of the clamp element. As drilling progresses, the rod passes through the aperture, thereby ensuring that drilling occurs along a predetermined drilling path extending along the bone axis.

17 Claims, 2 Drawing Sheets

DRILL ALIGNMENT GUIDE FOR OSTEOPLASTIC SURGERY

BACKGROUND OF THE INVENTION

The present invention is directed to devices useful in osteoplastic surgical procedures. More particularly, the invention is directed to a drill alignment guide which is useful in the revision of a total hip replacement.

As a result of advancements in medical technology, the surgical replacement of dysfunctional joints has become common. One such surgical replacement operation, referred to as a total hip replacement, is performed on the ball and socket joint of the hip. However, the long term success of these total hip replacements has been limited because the active life span of the artificial joint recipient often exceeds the life span of the artificial joint itself. Thus, for the recipient to lead a normal life, it is often necessary to perform a revision, i.e. replacement, of the artificial hip joint.

In the course of revision surgery, it is necessary to remove the worn ball joint and its supporting shaft, from within the intramedullary canal of the femur. The cement material used to anchor the shaft of the original replacement ball to the femur must be removed from the intramedullary canal as well. Typically, the cement is broken up and removed by axially drilling within the intramedullary canal. During such drilling procedures, it is important that the drill be properly aligned and guided to avoid accidental perforation of the cortex of the femur.

There are at least two techniques which are utilized in the prior art to guide the drill within the intramedullary canal. One such technique simply is to guide the drill manually by estimating the location of the drill burr in relation to the center of the intramedullary cortex. When the drill is guided by this freehand technique it is quite possible that the cortex could be accidentally perforated. Fluoroscopy is another technique which is used to guide the drill along a predetermined path in order to avoid unexpected damage to the femur. This technique is disfavored, however, as it may expose the patient to a high dosage of radiation. Also, the typically large size of the fluoroscopy equipment may occupy too much space and may compromise the sterility of the operating room.

Accordingly, it is an object of the present invention to provide an apparatus which accurately guides a drill along a path within the intramedullary canal of a femur. A further object of the invention is to provide a drill alignment apparatus which may be safely and conveniently used in a surgical environment. Other objects of the invention will be apparent to those having ordinary skill in the art upon reading the present disclosure.

SUMMARY OF THE INVENTION

The present invention is an alignment apparatus for surgical drills useful in the revision of a total hip replacement. The alignment apparatus enables the drill to be guided along a predetermined drilling path within the intramedullary canal of a femur from which bonding cement must be removed, without damage to the cortex of the femur.

The drill alignment apparatus is adapted for use with a drill having a handle and an elongated drill shaft extending along a drill axis and having a drill burr secured to one end thereof or an equivalent device. The drill alignment apparatus includes a drill alignment rod which is secured to the drill handle and disposed substantially parallel to and located a predetermined distance from the drill axis. The rod extends forwardly of the drill handle. The drill alignment apparatus also includes a clamp apparatus having at one end a gap of a predetermined width which is defined by two tines. The gap and the tines are adapted to interferingly engage the shaft of the femur. The opposite end of the clamp features a centrally disposed aperture for receiving and permitting free passage of the alignment rod therethrough.

The alignment apparatus of the present invention is used by interferingly fitting the shaft of a femur within the gap of the clamp so that the clamp extends in a plane perpendicular to the longitudinal axis of the femur. The central axis of the aperture within the clamp is displaced by a predetermined distance from the femur axis. The forward end of the alignment rod, positioned parallel to the drill shaft, is then slidingly positioned within the aperture of the clamp. The surgeon may then commence drilling within the intramedullary canal of the femur by applying appropriate pressure against the drill handle, while simultaneously initiating rotation of the drill shaft and burr. As the drilling continues, the drill burr is guided along a desired drilling path within the intramedullary canal of the femur as the alignment rod extends through the clamp aperture. The Positioning of the alignment rod within the clamp aperture helps to ensure that the drill shaft does not stray from the desired path to an extent that damage to the femur could occur.

In one embodiment of the invention, the clamp apparatus comprises a single plate having a thickness of approximately 2 to 5 mm. Preferably, however, the clamp of the present invention is constructed of two identically shaped plates, each having a thickness of approximately 2 to 5 mm. The plates are spaced apart by about 0.5 to 5.0 cm and joined together by a suitable fastening means thus forming a double plate clamp structure.

BRIEF DESCRIPTION OF THE DRAWINGS

For a fuller understanding of the nature and objects of the invention, reference should be made to the following detailed description and the accompanying drawings, in which.

DETAILED DESCRIPTION OF THE INVENTION

Figure 1:
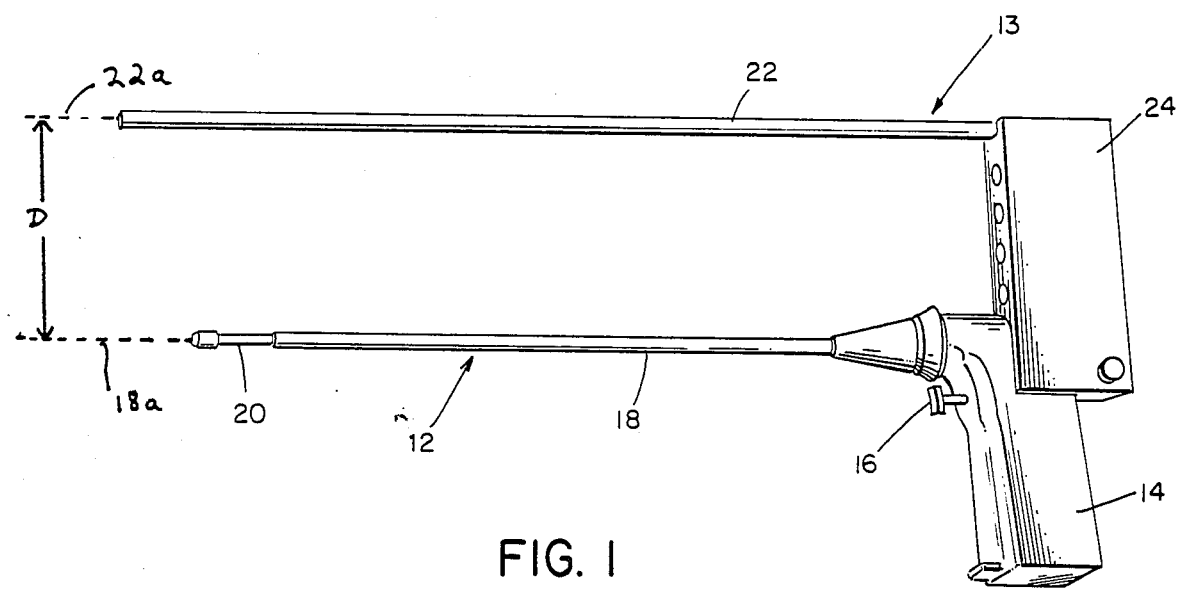
FIG. 1 is a side perspective view of a drill with attached alignment apparatus of the present invention.

FIGS. 1 through 4, show a conventional drill 12 together with an alignment apparatus 13 of the present invention. The drill 12 includes a housing handle 14, having a trigger mechanism 16 for actuating the drill. In addition, a drill shaft 18 extends forwardly from handle 14 along a drill axis 18a. A cutting element, drill burr 20, is removably attached to the forward end of shaft 18.

The drill alignment apparatus 13 (best shown in FIG. 4) comprises an alignment rod 22 and clamp apparatus (not shown in FIG. 1). The alignment rod 22 is secured to an upper portion of handle 14 by way of an alignment rod support 24 so that the principal axis 22a of rod 22 is parallel to and displaced by distance D from axis 18a.

Figure 2A:
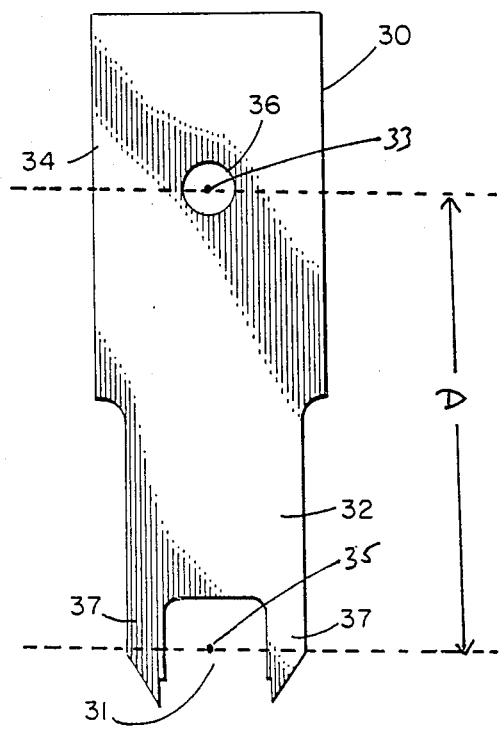
FIG. 2A is a front view of a single plate clamp apparatus for use with the alignment apparatus of FIG. 1.
Figure 2B:
FIG. 2B is a side view of the clamp shown in FIG. 2A.

FIGS. 2A and 2B illustrate one embodiment of the clamp apparatus in which clamp 30 is constructed of a single metal plate having a thickness of approximately 2 to 5 mm.

A bottom portion 32 of clamp 30 includes a region defining an open gap 31 adapted to interferingly engage the outer surface of the femur. As shown, the gap-defining region includes tines 37. A top portion 34 of clamp 30 is integral with bottom portion 32 and includes a centrally located aperture 36 for receiving the alignment rod 22. The center point 35 of gap 31 is separated by distance D from the center point 33 of aperture 36.

Figure 3A:
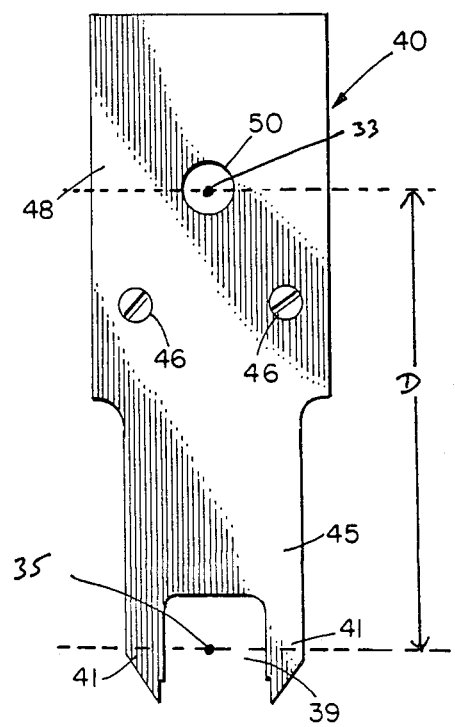
FIG. 3A is a front view of a clamp apparatus having a dual plate construction.
Figure 3B:
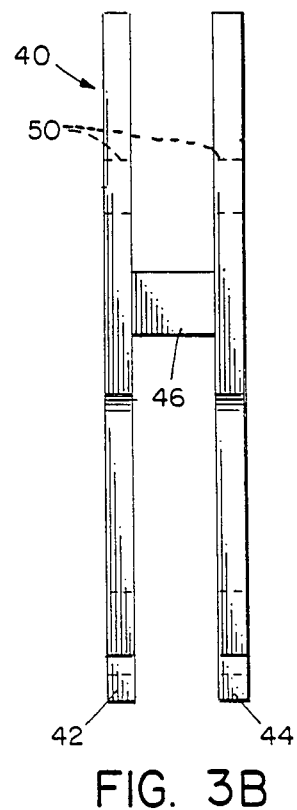
FIG. 3B is a side view of the clamp shown in FIG. 3A.

In a preferred embodiment, illustrated in FIGS. 3A and 3B, clamp 40 features a double plate construction. In this embodiment identically shaped plates 42 and 44 are spaced apart from one another by a distance of approximately 0.5-5.0 cm and joined together by a flange 46, or similar coupling member. In each of plates 42 and 44, an upper portion 48 is integral with bottom portion 45 and includes a centrally aligned aperture 50 which is adapted to receive alignment rod 22. The apertures 50 of plates 42 and 44 are coaxial. Each of plates 42 and 44 also include a gap 39 in lower portion 45. Gap 39 is defined by tines 41 which are adapted to interferingly engage the femur so that the center point 35 of gap 39 is offset by distance D from the center point 33 of aperture 50. In practice, a set of clamps may be maintained ready for use, each having gaps of different widths in order to accommodate different diameter femurs.

The drill 12 shown with the illustrated embodiment of the present invention may be of any type suitable for use in surgical procedures. A preferred drill features interchangeable drill burrs and drill shafts which vary in size to accommodate the requirements of any given operation. An example of a preferred drill is the Cebatome sold by the Hall Surgical, Divison of Zimmer, Inc. of Carpenteria, Calif.

As noted above, alignment rod 22 is affixed to the drill 12 by way of alignment rod support 24 which mounts to a top portion of the drill handle 14. Alignment rod 22 preferably is a rigid member constructed of metal or a rigid, durable polymer. The rod 22 may be disposed above the drill shaft 18 by a distance of approximately 5.0 to 15.0 cm. The length of rod 22 may vary to accommodate femurs of different sizes, but, in any event, should be of sufficient length to extend through the aperture 36 of clamp 30 (or apertures 50 of clamp 40) by several centimeters before drilling is commenced. Preferably, the rod 22 is approximately 30%-40% longer than the combined length of the drill burr 20 and drill shaft 18. By way of example, the drill alignment apparatus of the present invention may be used with interchangeable alignment rods 22 of at least three different lengths. For example, rod 22 having a length of approximately 9 inches may be used with a drill shaft of 5 3/16 inches, an 18 inch rod with a 10 11/16 inch shaft and a 23 inch rod with a 13 11/16 shaft.

Clamps 30 and 40 of the illustrated embodiments may be constructed of a rigid, sterilizable metallic material, such as stainless steel, or other suitable materials, including polymers. The size of gap 31 (or 39) should be substantially the same as the diameter of the femur through which drilling will occur in order to accommodate an interference fit between the clamp and the femur. Thus, a preferred drill alignment apparatus will include clamps of different sizes with gaps ranging in size from approximately 2.5 cm to 8 cm. Apertures 36 and 50 of clamp 30 and 40, respectively, are adapted to receive rod 22 and preferably may be of a diameter approximately 1.1 to 1.5 times greater than the diameter of rod 22.

Apertures 36 and 50 are positioned on clamps 30 and 40 such that, when affixed to the shaft of the femur, the center of the aperture 33 will be at a height above the center of the intramedullary canal of the femur which is equal to the distance (D) by which rod axis 22a is disposed above shaft 18. In a currently preferred embodiment rod 22 is disposed 4.25 inches above shaft axis 18a while the center points 33 of apertures 36 and 50 are positioned 4.25 inches above the center points 35 of at the gaps 31 and 39, which are substantially coaxial with the central axis of the intramedullary canal of the engaged femur.

Figure 4:
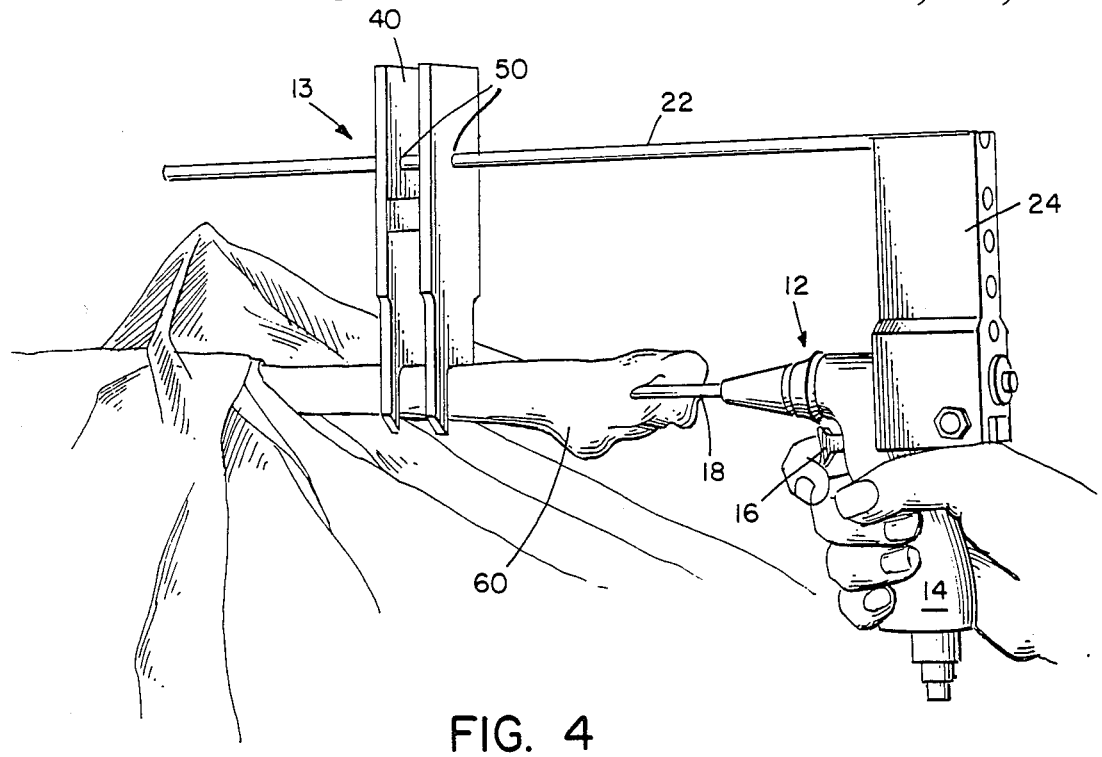
FIG. 4 is a perspective view of the drill alignment guide as it is utilized during surgery.

The drill alignment apparatus of the present invention may be used in the manner illustrated in FIG. 4. Clamp apparatus 40 is initially clamped (i.e., secured) to the femur 60 by way of an interference fit. Preferably, the clamp 40 will be positioned a distance from the top end of the intramedullary canal which is slightly less than the combined length of the drill burr 20 and shaft 18. The drill burr 20 may then be positioned in the center of the intramedullary canal, at the top opening thereof. Simultaneously, the forward end of rod 22 is directed through apertures 50 of clamp 40. Once the drill is properly aligned in this manner, the surgeon may activate the drill and commence the drilling procedure. As the drill burr is directed into the intramedullary canal, it is maintained on a drill path which substantially coincides with the center of the intramedullary canal of the femur due to the interaction of alignment rod 22 with apertures 50 of clamp 40.

Clamps 30 and 40 of FIGS. 2A and 2B and FIGS. 3A and 3B, respectively, typically may be constructed of metal plates of sufficient strength to avoid distortion of the clamp during its use. The length and width of the clamps 30 and 40 may, of course, vary. One of ordinary skill in the art may easily design a suitable clamp having the appropriate length and width for a given application.

Although particular embodiments of this invention have been described and are illustrated herein, it is recognized that modifications and variations may readily occur to those skilled in the art. For example, although the present invention is described with respect to its application in drilling within the femur, it is also applicable to drill alignment involving surgery on the proximal tibia, distal femur and the like. Consequently, it is intended that the claims be interpreted to cover such modifications and equivalents.

What is claimed is:

1. A drill alignment apparatus for guiding along a predetermined drilling path a drill having an elongated drill shaft extending along a drill axis from a housing assembly, said shaft having a cutting element disposed at its distal end, said alignment apparatus comprising:
(A) an alignment rod secured to said housing assembly and extending along a rod axis, said rod axis being spaced a predetermined distance (D) from said drill axis and oriented substantially parallel thereto; and (B) a clamp element having at one end an aperture for permitting the passage therethrough of said alignment rod along said rod axis, and having at its other end a clamping means for clamping said clamp element to a bone with said drill axis being substantially coaxial with the central axis of the intramedullary canal of the bone when the alignment rod is positioned within the aperture.

2. The drill alignment apparatus of claim 1 wherein the clamp element includes at least one elongated rigid plate member having said aperture at one end, and wherein said clamping means includes a region defining an open gap at the other end, the gap defining region being adapted for interfering engagement with the bone, with the central axis of the bone being spaced from the central axis of the aperture by predetermined distance (D).

3. The apparatus of claim 2, wherein the rod is secured to a top end of a support means, which, in turn, is secured to the handle of the drill.

4. The apparatus of claim 3, wherein the length of the rod is greater than the length of the drill shaft.

5. The apparatus of claim 4, wherein the rod is disposed approximately 5.0 to 15.0 centimeters above the drill shaft.

6. The apparatus of claim 5, wherein the first end of said clamp means comprises two tines separated by a gap, said tines and said gap being adapted such that the tines may interferingly engage the shaft of a bone enabling the clamp means to protrude from and be aligned perpendicularly to the shaft of the bone.

7. The apparatus of claim 6, wherein said clamp means comprises a single plate.

8. The apparatus of claim 6, wherein said clamp means comprises two plates joined together and separated by approximately 1.5 to 7 centimeters, each of said plates having a pair of tines separated by a gap.

9. The apparatus of claim 8, wherein the bone is a femur.

10. The apparatus of claim 9, wherein said aperture has a diameter which is approximately 1.1 to 1.5 times greater than the diameter of the rod.

11. The apparatus of claim 10 wherein the center of the aperture is disposed a distance above the center axis of the gap region, which is substantially equal to the distance which the central axis of the alignment rod is disposed above the central axis of the drill shaft.

12. The apparatus of claim 11 wherein said drill is adapted to drill within the intramedullary canal of a bone.

13. The apparatus of claim 12, wherein said drill burr is adapted to remove cement from the intramedullary canal of the femur.

14. The method of guiding a drill burr along a predetermined drill path through the center of the intramedullary canal of a bone, comprising the steps of:

a. affixing a clamp means having a first end adapted to engage a bone and a second end having an aperture disposed a predetermined distance above the center of the intramedullary canal;

b. providing a drill having a handle with an elongate drill shaft extending therefrom and drill burr attached thereto, said drill also having an alignment rod disposed a predetermined distance above the drill shaft and oriented parallel thereto;

c. aligning the alignment rod within the aperture; and d. drilling through the intramedullary canal of the bone while guiding the alignment rod through the aperture.

15. The method of claim 14, wherein the drill burr is directed along the longitudinal axis of the intramedullary canal without perforating the cortex of the bone.

16. The apparatus of claim 15, wherein said bone is a femur.

17. The method of claim 16, wherein the drilling procedure is performed during revision total hip replacement surgery.

* * * * *